(12) United States Patent
Myers et al.

(10) Patent No.: US 8,927,799 B2
(45) Date of Patent: Jan. 6, 2015

(54) PROPANE DEHYDROGENATION PROCESS UTILIZING FLUIDIZED CATALYST SYSTEM

(75) Inventors: David N. Myers, Hoffman Estates, IL (US); Daniel N. Myers, Arlington Heights, IL (US); Joseph E. Zimmermann, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 802 days.

(21) Appl. No.: 12/916,969

(22) Filed: Nov. 1, 2010

(65) Prior Publication Data

US 2012/0108877 A1    May 3, 2012

(51) Int. Cl.
*C07C 5/333* (2006.01)

(52) U.S. Cl.
CPC ............... *C07C 5/333* (2013.01); *C07C 5/3332* (2013.01)
USPC ............ 585/659; 585/654; 585/655; 585/661

(58) Field of Classification Search
CPC .. C07C 5/333; C07C 5/3332; C07C 2521/06; C07C 11/06
USPC .......................... 585/654, 655, 659, 661, 662
See application file for complete search history.

(56) References Cited

U.S. PATENT DOCUMENTS

| | | | |
|---|---|---|---|
| 2,962,362 A * | 11/1960 | Moorman | 422/142 |
| 3,050,469 A * | 8/1962 | Morgan et al. | 502/12 |
| 4,310,440 A | 1/1982 | Wilson et al. | |
| 4,440,871 A | 4/1984 | Lok et al. | |
| 4,554,154 A | 11/1985 | White | |
| 4,752,651 A | 6/1988 | Kaiser | |
| 4,793,984 A | 12/1988 | Lok et al. | |
| 4,853,197 A | 8/1989 | Wilson et al. | |
| 5,414,168 A * | 5/1995 | Scott | 585/2 |
| 5,457,256 A * | 10/1995 | Mitariten et al. | 585/655 |
| 6,218,589 B1 * | 4/2001 | Cottrell | 585/324 |
| 6,362,385 B1 * | 3/2002 | Iezzi et al. | 585/661 |
| 2004/0092391 A1 * | 5/2004 | Rokicki et al. | 502/308 |
| 2008/0161624 A1 * | 7/2008 | Glover et al. | 585/634 |
| 2009/0321318 A1 | 12/2009 | Pan et al. | |
| 2009/0325784 A1 * | 12/2009 | Pan et al. | 502/56 |
| 2010/0331589 A1 | 12/2010 | Zimmermann | |

* cited by examiner

*Primary Examiner* — In Suk Bullock
*Assistant Examiner* — Bradley Etherton

(57) ABSTRACT

A process for the production of propylene from a propane rich hydrocarbon source is presented. The process converts a propane rich stream and uses less equipment and energy for the separation and production of propylene. The process uses a non-noble metal catalyst and utilizes a continuous reactor-regeneration system to keep the process on line for longer periods between maintenance.

20 Claims, 1 Drawing Sheet

PROPANE DEHYDROGENATION PROCESS UTILIZING FLUIDIZED CATALYST SYSTEM

FIELD OF THE INVENTION

The field of the invention is production of light olefins. In particular, the invention relates to the dehydrogenation of paraffins in the C3 to C5 range.

BACKGROUND OF THE INVENTION

Ethylene and propylene are light olefin hydrocarbons with two or three atoms per molecule, respectively, and are important chemicals for use in the production of other useful materials, such as polyethylene and polypropylene. Polyethylene and polypropylene are two of the most common plastics found in use today and have a wide variety of uses for both as a material fabrication and as a material for packaging. Other uses for ethylene and propylene include the production of vinyl chloride, ethylene oxide, ethylbenzene and alcohol. Steam cracking or pyrolysis of hydrocarbons produces essentially all of the ethylene and propylene. Hydrocarbons used as feedstock for light olefin production include natural gas, petroleum liquids, and carbonaceous materials including coal, recycled plastics or any organic material.

A light olefin plant is a very complex combination of reaction and gas recovery systems. The feedstock is charged to a cracking zone in the presence of steam at effective thermal conditions to produce a pyrolysis reactor effluent gas mixture. The pyrolysis reactor effluent gas mixture is stabilized and separated into purified components through a sequence of cryogenic and conventional fractionation steps. A typical light olefin plant includes an ethylene separation section containing both cryogenic and conventional fractionation steps to recover an ethylene product with a purity exceeding 99.5% ethylene. Propylene and heavier hydrocarbons are separated from the ethylene and recovered in a separate section, or separate fractionation column.

Simplification of the process can save energy, and capital cost, while increasing the overall yields of product.

SUMMARY OF THE INVENTION

The invention provides a process for the production of propylene from propane rich feedstocks. The propane rich feedstock is passed through a dryer to provide for a dry propane rich feedstream. The dried feedstream is preheated through a heat exchanger to preheat the feed to the reactor temperature. The feedstream enters a dehydrogenation reactor wherein the reactor has a circulating catalyst stream. In the reactor the propane rich hydrocarbon stream is dehydrogenated to create an intermediate process stream having propylene. The process stream is cooled and compressed, and separated to create a first process stream comprising C2 and lighter gases, and a second process stream comprising C3 and heavier components. The second stream is passed to a propylene-propane splitter to provide a propylene product stream. The propane and heavier components are passed back to the dehydrogenation reactor for further dehydrogenation.

The reactor has a catalyst for the continuous addition of regenerated catalyst and a catalyst outlet for the continuous withdrawal of spent catalyst. The spent catalyst is passed to a regeneration unit, where the catalyst is regenerated. The spent catalyst is heated in a combustion zone of the regenerator to burn off carbon deposits on the catalyst with an oxidizing gas and fuel creating a regenerated catalyst flue gas stream. The catalyst is separated from the flue gas and passed to a stripping zone. The regenerated catalyst is stripped of residual oxygen and then the regenerated catalyst is returned to the reactor.

Additional objects, embodiments and details of this invention can be obtained from the following drawing and detailed description of the invention.

DETAILED DESCRIPTION OF THE INVENTION

Figure 1:
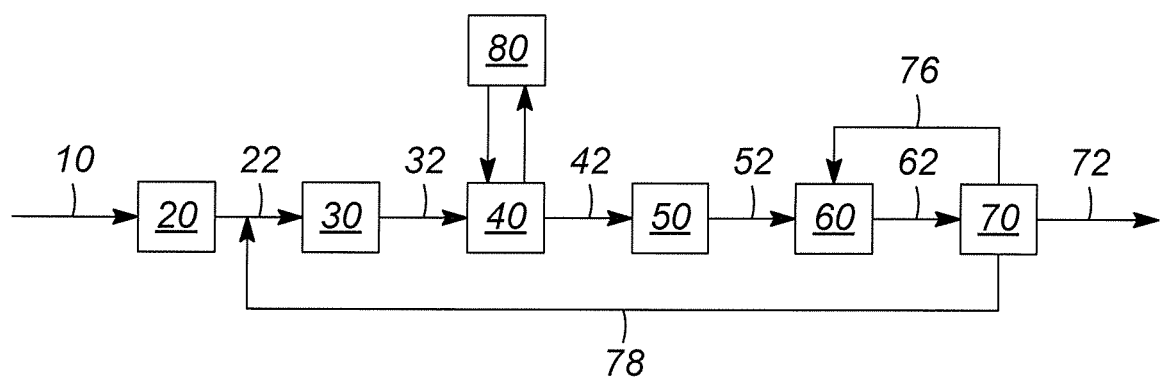
FIG. 1 is a diagram of the process.

Currently, the production of propylene is primarily from the normal sources of light olefins that are produced through the cracking process of heavier hydrocarbons such as naphtha or vacuum gas oil (VGO), which are produced under high severity FCC applications. Propylene is subsequently separated out from a product stream comprising ethylene and propylene. There is a growing gap between the production of propylene and the demand for propylene. The demand is being met through dedicated processes that use light paraffinic feedstocks, and directly convert the paraffins to olefins through dehydrogenation. The feedstock of choice is propane or an LPG feed, which can be directly dehydrogenated and overcomes drawbacks of other methods of propylene production, such as methanol to olefins and the cracking of heavier hydrocarbons.

The production of propylene using a process for the direct conversion of a propane feedstream to propylene typically utilizes a noble metal catalyst or chromium type catalyst. The dehydrogenation process is endothermic, and in one current process utilizes a plurality of reactor beds with interstage heating between the reactor beds. The reheating of the effluent from one reactor before passing to a subsequent reactor allows for continuous processing. The catalyst develops a coke buildup during the dehydrogenation process, and must be regenerated. A continuous process includes the ability to continuously regenerate the catalyst in the reactors.

The process is for the production of propylene and is shown in the FIG. 1. The process includes passing a hydrocarbon gas 10 that is rich in propane through a dryer 20 to create a dry hydrocarbon stream 22. The dried stream 22 is passed to a heat exchanger 30 to cool the reactor products and preheat the feed. The preheated feed is passed to a dehydrogenation reactor 40 to generate an intermediate stream rich in propylene 42. The present invention does not need to incorporate a depropanizer, as the heavier hydrocarbons can be handled by the reactor design and operating conditions of the present invention. However, a depropanizer may be included dependent upon the composition of heavier hydrocarbons in the feedstock. The intermediate stream 42 is compressed, dried and cooled in a treatment section 50 before passing the treated stream 52 to an optional selective hydrogenation reaction zone 60. In one embodiment, the treatment section consists of driers for the intermediate stream 42. The selective hydrogenation zone 60 converts dienes and acetylenes to olefins to create a hydrogenated stream 62. The hydrogenated stream 62 is passed to a separation unit 70 wherein the propylene is recovered as a propylene product stream 72.

The separation unit 70 where includes a deethanizer to separate C2 and lighter gases from the C3 hydrocarbon stream. The deethanizer bottoms passed to a propylene-propane splitter. The C2 and lighter gases can also be passed to a pressure swing adsorber, to recover the hydrogen. A portion of the hydrogen 76 can be passed to the selective hydrogenation reactor 60 for use in selective hydrogenation of dienes and acetylenes.

The process can further include passing the propane rich bottoms stream 78 from the propylene-propane splitter to mix with the dry hydrocarbon feed stream 22. C4 and heavier hydrocarbons do not need to be separated from the C3 stream, as they will be recycled back to the dehydrogenation unit. However, depending on the feedstock composition, in the presence of relatively large amounts of C4 and heavier hydrocarbons, the process stream can be passed through a depropanizer, with the heavier hydrocarbons passed to other process units, or recycled to the dehydrogenation reactor. A depropanizer, when added, will be located in the separation unit 70.

The process includes a dehydrogenation reactor 40 having two reaction zones. There is a lower combustor zone and an upper reaction zone. The lower combustor zone is a fluidized bed, and is operated at flow conditions of gas and catalyst to maintain an average reactor bed density between 65 kg/m$^3$ and 400 kg/m$^3$. A preferred operation is for the bed density to be between 150 kg/m$^3$ and 250 kg/m$^3$, with a more preferred bed density between 160 kg/m$^3$ and 200 kg/m$^3$. The lower combustor zone is operated to maintain a superficial gas flow velocity between 0.9 m/s and 2.5 m/s.

Catalyst is recirculated from the upper vessel to the combustor to maintain density. The catalyst is recirculated to provide a density of the combined gas and catalyst between 60 kg/m$^3$ and 380 kg/m$^3$ in the reactor. Preferably the density of the combined gas and catalyst is between 80 kg/m$^3$ and 300 kg/m$^3$ in the reactor combustor. A more preferred density is between 14 kg/m$^3$ and 240 kg/m$^3$, with a most preferred density maintained between 16 kg/m$^3$ and 200 kg/m$^3$. The gas velocity is preferably maintained at 1.5 m/s for mixing.

The upper reaction zone is a region where the catalyst is separated from the process stream, and creates a spent catalyst stream and a product stream. The upper reaction zone is operated to maintain a superficial gas velocity between 0.6 m/s and 1.2 m/s, and is operated at a pressure between 170 kPa and 240 kPa (absolute), with a preferred pressure approximately 200 kPa.

The spent catalyst is passed to a catalyst stripping section to remove residual hydrocarbons from the spent catalyst, and in particular to remove residual product or olefins. The stripping section can use a fuel gas as the stripping medium.

In one embodiment, the dehydrogenation reactor is a fluidized bed reactor, where the reactor has a catalyst inlet and a catalyst outlet. The process includes passing regenerated catalyst to the reactor through the catalyst inlet, and spent catalyst is withdrawn from the catalyst outlet. The spent catalyst is passed to a regeneration reactor, where the catalyst is regenerated. Regeneration typically comprises combusting the carbon deposits on the catalyst to create a regenerated catalyst stream. The regenerated catalyst is heated in a combustion zone of the regenerator. The regenerated catalyst is separated from the combustion gas products, to create the regenerated catalyst stream and a flue gas stream, before returning the catalyst to the dehydrogenation reactor.

Another embodiment of the invention is a process for the production of propylene. The process includes passing a hydrocarbon gas 10 rich in propane through a dryer 20 to remove water and create a dry hydrocarbon gas stream 22. The dried gas stream 22 is preheated through a heat exchanger 30 with a process gas from one of the process units. The preheated gas stream 32 is passed to a dehydrogenation reactor 40. The dehydrogenation reactor 40 circulates catalyst through a catalyst inlet to the reactor 40 from a regenerator 80, and returns spent catalyst through a reactor catalyst outlet to the regenerator 80. The catalyst is heated in a combustion zone of the regenerator reactor 80 and carbon deposits on the catalyst are burned off with an oxidizing gas and supplemental fuel, to create a stream comprising catalyst and flue gas. The catalyst and flue gas are separated, and the regenerated catalyst is passed to a catalyst stripper to remove residual oxygen adsorbed onto the catalyst, and then returned to the dehydrogenation reactor 40, and the flue gas is directed to the atmosphere after catalyst and heat recovery. The stripping gas is a dry inert gas, without any significant amount of oxygen in the gas.

A propylene product stream 42 is generated by the dehydrogenation reactor 40. The propylene stream 42 is treated and compressed and cooled. The compressed and treated stream 52 is passed to an optional selective hydrogenation reaction section 60 to remove diolefins and acetylenes, to create a product stream 62 having a reduced diolefin composition. The product stream 62 is recovered in a light olefin recovery unit 70 to generate a propylene product stream 72. A propane stream is created during the recovery of the propylene product stream 72. The propane stream is passed back to the dehydrogenation unit 30 and is mixed with the dry hydrocarbon gas stream 22. Light gases, comprising C2 and lighter gases, separated in the olefin recovery unit 70 can be further separated to recover a hydrogen stream, and a tail gas stream. A portion of the hydrogen stream can be passed to the optional selective hydrogenation reactor 60 for converting the diolefins. This process does not require the addition of external sources of hydrogen. In one embodiment, the propane stream is passed to a depropanizer. The depropanizer is used when the feedstock composition leads to a significant amount of C4 and heavier hydrocarbons. The depropanizer is then used to separate the C4 and heavier hydrocarbons from the propane stream before passing the propane stream to the propylene/propane splitter.

Some dehydrogenation processes use a noble metal catalyst. The catalyst used in this process is a non-noble metal catalyst. The catalyst comprises small particles that are in the range of approximately 75 micrometers.

During the process of dehydrogenation of paraffins, the catalyst accrues a coke buildup over time. The coke buildup eventually adversely affects the catalyst performance and the catalyst needs to be regenerated. The catalyst is cycled through a continuous catalyst regenerator as part of the system for the paraffin dehydrogenation. Simple air-burn regeneration returns fresh catalyst performance. The regeneration can take place at ambient pressure using air, or can be at higher pressures using air, or another oxidation agent, such as oxygen, although air is preferred.

Another choice for the catalyst is a metal oxide stabilized zirconia. The metal in the metal oxide for stabilization can include metals such as scandium, yttrium, lanthanum, cerium, actinium, calcium, and magnesium.

The present invention does not utilize recycle hydrogen for the reaction to proceed. This means no hydrogen is needed at the inlet for a hydrogen to hydrocarbon ratio of zero at the inlet to the dehydrogenation reactor.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the production of propylene comprising:
    passing a hydrocarbon gas rich in propane through a dryer, thereby creating a dry hydrocarbon gas stream;
    passing the hydrocarbon gas stream through a heat exchanger thereby creating a preheated hydrocarbon feedstream;
    passing the preheated hydrocarbon feedstream to a dehydrogenation reactor, wherein the dehydrogenation reactor is a fluidized bed reactor with a catalyst inlet and a catalyst outlet, wherein regenerated catalyst is passed to the reactor through the catalyst inlet and spent catalyst is passed out of the reactor through the catalyst outlet, thereby creating an intermediate hydrocarbon stream comprising propylene, wherein no hydrogen is recycled to the dehydrogenation reactor and the hydrogen to hydrocarbon ratio is zero at the inlet to the dehydrogenation reactor, and wherein the dehydrogenation reactor utilizes a catalyst comprising zirconia;
    compressing and treating the intermediate hydrocarbon stream, thereby creating a compressed hydrocarbon stream;
    cooling the compressed hydrocarbon stream; and
    separating cooled compressed hydrocarbon stream thereby recovering a propylene stream.

2. The process of claim 1 wherein the separation of the cooled compressed hydrocarbon stream comprises:
    passing the hydrocarbon stream to a deethanation column, thereby creating an overhead stream comprising C2 and lighter gases, and a bottoms stream comprising C3 hydrocarbons; and
    passing the bottoms stream to a propane-propylene splitter, thereby creating a propylene rich product overhead stream and a propane rich bottoms stream.

3. The process of claim 2 further comprising passing the cooled compressed hydrocarbon stream to a selective hydrogenation reactor.

4. The process of claim 3 further comprising:
    passing the C2 and lighter gases to a pressure swing adsorber, thereby generating a hydrogen stream; and
    passing a portion of the hydrogen stream to the selective hydrogenation reactor.

5. The process of claim 2 further comprising passing the propane rich bottoms stream to mix with the dry hydrocarbon gas stream.

6. The process of claim 1 wherein the dehydrogenation reactor comprises two zones, a lower combustor zone and an upper reaction zone.

7. The process of claim 6 wherein the combustor zone is a fluidized bed.

8. The process of claim 6 wherein the combustor zone is operated to maintain an average reactor bed density between 65 kg/m3 to 400 kg/m3.

9. The process of claim 6 wherein the combustor zone is operated to maintain a superficial velocity between 0.9 m/s to 2.5 m/s.

10. The process of claim 6 wherein the upper reaction zone separates catalyst from a process stream thereby creating a spent catalyst stream and a product stream.

11. The process of claim 6 wherein the spent catalyst is passed to a catalyst stripping section, and the spent catalyst is stripped of residual product.

12. The process of claim 11 wherein the stripping section uses a fuel gas as the stripping medium.

13. The process of claim 6 wherein the upper reaction zone is operated with a superficial velocity between 0.6 m/s to 1.2 m/s.

14. The process of claim 6 wherein the upper reaction zone is operated at a pressure between 170 kPa to 240 kPa.

15. The process of claim 1 further comprising:
    passing the spent catalyst to a regenerator reactor, thereby creating
    passing the spent catalyst to a regenerator reactor, thereby creating the regenerated catalyst stream and passing the regenerated catalyst to the dehydrogenation reactor;
    heating the spent catalyst in a combustion zone of the regenerator reactor and combusting carbon deposits on the catalyst with an oxidizing gas and fuel, thereby creating a regenerated catalyst and flue gas stream;
    separating the regenerated catalyst stream into a flue gas stream and a regenerated catalyst; and
    passing the regenerated catalyst to the dehydrogenation reactor catalyst inlet.

16. A process for the production of propylene comprising:
    passing a hydrocarbon gas rich in propane through a dryer, thereby creating a dry hydrocarbon gas stream;
    passing the hydrocarbon gas stream through a heat exchanger thereby creating a preheated hydrocarbon feedstream;
    passing the preheated hydrocarbon feedstream to a dehydrogenation reactor, wherein the dehydrogenation reactor has a catalyst inlet and a catalyst outlet, thereby creating an intermediate hydrocarbon stream comprising propylene, wherein there is no hydrogen at the inlet to provide a hydrogen to hydrocarbon ratio of zero at the inlet to the dehydrogenation reactor, and wherein the dehydrogenation reactor utilizes a catalyst comprising a metal oxide stabilized zirconia;
    compressing and treating the intermediate hydrocarbon stream, thereby creating a compressed hydrocarbon stream;
    cooling the compressed hydrocarbon stream;
    separating cooled compressed hydrocarbon stream thereby recovering a propylene stream and a light stream comprising C2 and lighter gases;
    passing spent catalyst from the dehydrogenation reactor outlet to a regenerator reactor;
    heating the spent catalyst in a combustion zone of the regenerator reactor and combusting carbon deposits on the catalyst with an oxidizing gas and fuel, thereby creating a regenerated catalyst flue gas stream;
    separating the regenerated catalyst flue gas stream into a flue gas stream and a regenerated catalyst stream;
    passing the regenerated catalyst to a regenerated catalyst stripper; and
    passing the stripped, regenerated catalyst to the dehydrogenation reactor catalyst inlet.

17. The process of claim 16 further comprising passing the cooled compressed hydrocarbon stream to a selective hydrogenation reactor.

18. The process of claim 16 wherein the cooled compressed hydrocarbon stream is separated into the propylene stream and a propane stream; and
    the propane stream is passed to mix with the dry hydrocarbon gas stream.

19. The process of claim 17 further comprising passing the light stream comprising C2 and lighter gases to a pressure swing adsorber, thereby creating a hydrogen stream and a tail gas stream; and
    passing a portion of the hydrogen stream to the selective hydrogenation reactor.

20. The process of claim 16 wherein the regenerated catalyst stripper uses a dry inert gas.

* * * * *